(12) United States Patent
Kanai et al.

(10) Patent No.: US 12,293,550 B2
(45) Date of Patent: May 6, 2025

(54) OUTPUT DEVICE, METHOD, AND NON-TRANSITORY COMPUTER READABLE RECORDING MEDIUM

(71) Applicant: PANASONIC HOLDINGS CORPORATION, Osaka (JP)

(72) Inventors: Hirofumi Kanai, Osaka (JP); Toshihide Mori, Osaka (JP); Yuka Yamada, Nara (JP); Hideyuki Maehara, Osaka (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 384 days.

(21) Appl. No.: 18/085,118

(22) Filed: Dec. 20, 2022

(65) Prior Publication Data

US 2023/0117389 A1  Apr. 20, 2023

Related U.S. Application Data

(63) Continuation of application No. PCT/JP2021/019028, filed on May 19, 2021.
(Continued)

(51) Int. Cl.
*G06T 7/90* (2017.01)
*G06T 7/00* (2017.01)
(Continued)

(52) U.S. Cl.
CPC .............. *G06T 7/90* (2017.01); *G06T 7/0016* (2013.01); *G06T 7/62* (2017.01); *G06V 10/25* (2022.01);
(Continued)

(58) Field of Classification Search
CPC ........... G06T 7/90; G06T 7/0016; G06T 7/62; G06T 2207/10024; G06T 2207/30004;
(Continued)

(56) References Cited

U.S. PATENT DOCUMENTS

2017/0303901 A1  10/2017  Sekine
2019/0195802 A1*  6/2019  Attar .................... G01N 21/645
(Continued)

FOREIGN PATENT DOCUMENTS

JP  2016-004005  1/2016

OTHER PUBLICATIONS

International Search Report (ISR) from International Searching Authority (Japan Patent Office) in International Pat. Appl. No. PCT/JP2021/019028, dated Aug. 3, 2021, together with an English language translation.

*Primary Examiner* — Ali Bayat
(74) *Attorney, Agent, or Firm* — GREENBLUM & BERNSTEIN, P.L.C.

(57) ABSTRACT

An output device performs: acquiring a plurality of images chronologically captured by a camera located to photograph an inside of a bowl of a toilet; extracting, from the acquired images, an excrement image showing excrement; extracting, from the acquired images, a blood image showing a blood spot; determining, based on time information about the excrement image, an excretion start time; determining, based on time information about the blood image, a blood appearance start time, and determining, based on the blood image, a blood size indicating a size of the blood spot; generating, as excretion information, information including the excretion start time, the blood appearance start time, and the blood size; and outputting the generated excretion information.

12 Claims, 10 Drawing Sheets

Related U.S. Application Data

(60) Provisional application No. 63/044,747, filed on Jun. 26, 2020.

(51) Int. Cl.
*G06T 7/62* (2017.01)
*G06V 10/25* (2022.01)

(52) U.S. Cl.
CPC ............... *G06T 2207/10024* (2013.01); *G06T 2207/30004* (2013.01)

(58) Field of Classification Search
CPC ...... G06T 7/0012; G06V 10/25; G06V 10/56; G06V 20/52; G01N 33/483; G01N 33/50
USPC .......................................................... 382/128
See application file for complete search history.

(56) References Cited

U.S. PATENT DOCUMENTS

| | | | |
|---|---|---|---|
| 2019/0247650 A1* | 8/2019 | Tran ..................... | A61N 1/3704 |
| 2020/0008299 A1* | 1/2020 | Tran ..................... | H05K 1/0386 |
| 2020/0008786 A1* | 1/2020 | Sekine ...................... | E03D 9/00 |
| 2021/0389250 A1* | 12/2021 | Attar ...................... | G01N 21/31 |
| 2022/0221470 A1* | 7/2022 | Micallef ............ | G01N 33/6869 |
| 2023/0129932 A1* | 4/2023 | Wang ................... | G05D 1/0214 |
| | | | 4/321 |
| 2024/0057982 A1* | 2/2024 | Sekine ................... | G01N 21/84 |

\* cited by examiner

OUTPUT DEVICE, METHOD, AND NON-TRANSITORY COMPUTER READABLE RECORDING MEDIUM

TECHNICAL FIELD

This disclosure relates to a technology of outputting excretion information.

BACKGROUND ART

Patent Literature 1 discloses a technology of capturing images of faces having been excreted from a living body by a plurality of color cameras attached to a toilet seat before sinking into a water-seal portion, detecting the faces surface color from the captured images of the feces, and monitoring a change in the detected color to check an occult blood portion, thereby assisting in early detection of colorectal cancer.

However, Patent Literature 1 merely monitors a change in the color of the stool, and thus fails to distinguish breeding at excretion among bleeding attributed to an injury based on hemorrhoids, bleeding attributed to a problem in a digestive system, such as, a large intestine and a small intestine, and bleeding attributed a problem in a bladder or a urinary tract.

CITATION LIST

Patent Literature

Patent Literature 1: Japanese Unexamined Patent Publication No. 2016-4005

SUMMARY OF INVENTION

This disclosure has been achieved to solve the drawback described above, and has an object of providing a technology of outputting information necessary for determining whether bleeding at excretion derived from bleeding attributed to an injury around an anus, or bleeding attributed to a problem in a bladder, a urinary tract, or a digestive system.

An output device according to an aspect of the present disclosure is an output device for outputting excretion information. The output device includes: an acquisition part that acquires a plurality of images chronologically captured by a camera located to photograph an inside of a bowl of a toilet, each of the images including time information indicating a photographing time; a first extraction part that extracts, from the acquired images, an excrement image showing excrement; a second extraction part that extracts, from the acquired images, a blood image showing a blood spot; a first determination part that determines, based on time information about the excrement image, an excretion start time, when the first extraction part extracts the excrement image; a second determination part that determines, based on time information about the blood image, a blood appearance start time, and determines, based on the blood image, a blood size indicating a size of the blood spot, when the second extraction part extracts the blood image; and an output part that generates, as the excretion information, information including the excretion start time, the blood appearance start time, and the blood size, and outputs the generated excretion information.

DESCRIPTION OF EMBODIMENTS

Figure 1:
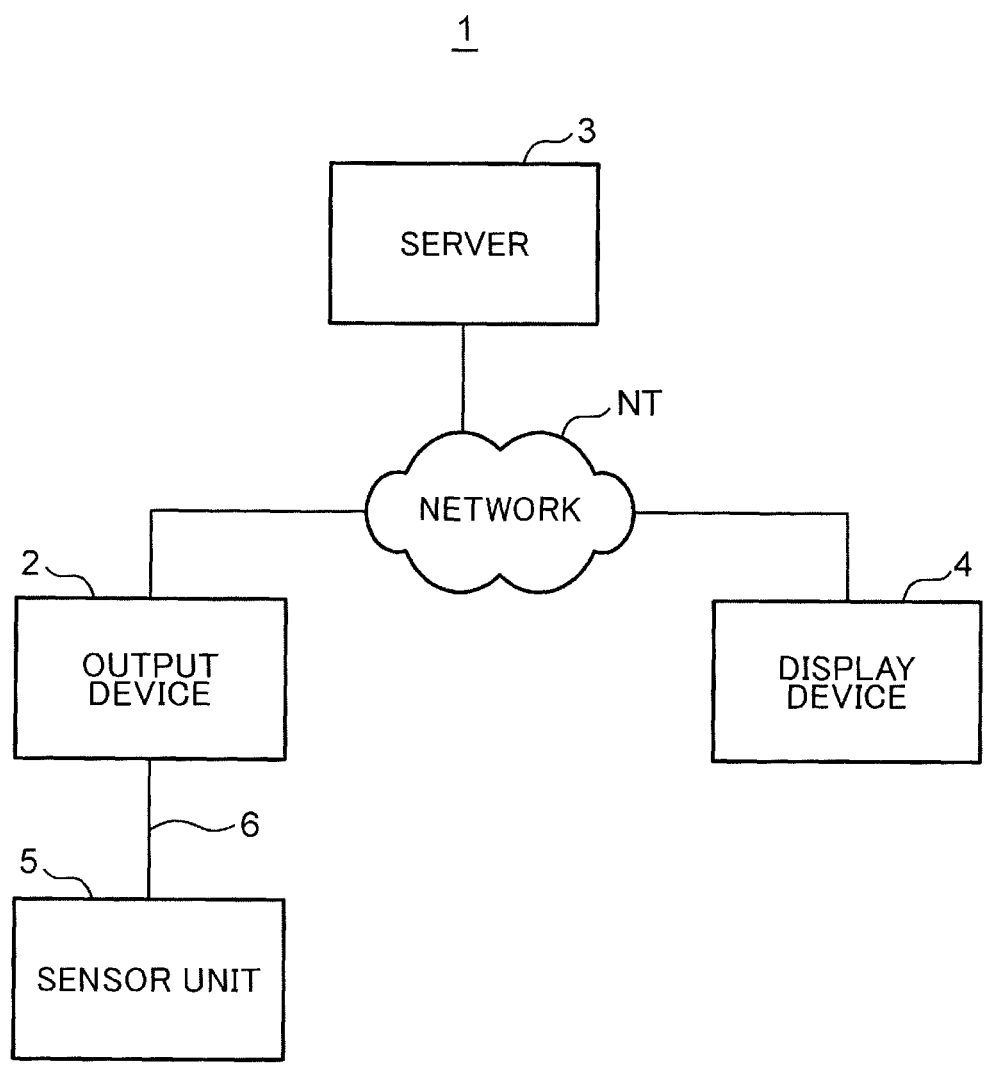
FIG. 1 is a block diagram showing an example of an overall configuration of an excrement management system in an embodiment of this disclosure.

Knowledge Forming the Basis of the Present Disclosure

In elderly care facilities and hospitals, management of a state of excrement of a user who uses such a facility is important for health maintenance of the user. In particular, regarding blood appearance or bleeding at excretion, early detection is significant in consideration of a possibility of a problem in a digestive system, such as a large intestine, a small intestine, and a duodenum.

However, blood appearance or bleeding at excretion is not limited to such bleeding attributed to a problem in the digestive system, and includes bleeding attributed to an injury around an anus like hemorrhoids. In this case, the bleeding attributed to such injury is not so much as serious as the bleeding attributed to the problem in the digestive system. Therefore, an exclusive determination on a problem in a digestive system on the blood appearance or the occurrence of bleeding may result in an inappropriate medical treatment and a trigger for unnecessary anxiety of a user. Distinction among types of breeding at excretion is important to avoid these risks.

When the digestive system has a problem, there is a feature that a large amount of blood accumulated in the digestive system flows out at once before stool is excreted from an anus. By contrast, in the case of an injury like hemorrhoids, there are features that blood falls after stool is excreted from the anus and further an amount of the blood is smaller than the amount of the blood relevant to the problem of the digestive system. This is because the breeding attributed to the injury occurs when the anus is injured by stool passing through the anus.

Moreover, when the bladder or the urinary tract has a problem, a large amount of blood flows at urination in some cases.

Patent Literature 1 monitors a change in a color of stool, but does not mention monitoring of an excretion start time, a blood appearance start time, and a blood size. Therefore, Patent Literature 1 fails to distinguish blood appearance or bleeding at excretion between bleeding attributed to an injury like hemorrhoids and bleeding attributed to a problem in a digestive system.

This disclosure has been achieved to solve the drawbacks described above, and has an object of providing a technology of outputting information necessary for determining whether blood appearance or bleeding at excretion derives from bleeding attributed to an injury around an anus, or bleeding attributed to a problem in a bladder, a urinary tract, or a digestive system.

An output device according to an aspect of this disclosure is an output device for outputting excretion information. The output device includes: an acquisition part that acquires a plurality of images chronologically captured by a camera located to photograph an inside of a bowl of a toilet, each of the images including time information indicating a photographing time; a first extraction part that extracts, from the acquired images, an excrement image showing excrement; a second extraction part that extracts, from the acquired images, a blood image showing a blood spot; a first determination part that determines, based on time information about the excrement image, an excretion start time, when the first extraction part extracts the excrement image; a second determination part that determines, based on time information about the blood image, a blood appearance start time, and determines, based on the blood image, a blood size indicating a size of the blood spot, when the second extraction part extracts the blood image; and an output part that generates, as the excretion information, information including the excretion start time, the blood appearance start time, and the blood size, and outputs the generated excretion information.

According to this configuration, a plurality of images chronologically captured by the camera located to photograph the inside of the bowl of the toilet is acquired. An excrement image showing excrement is extracted from the acquired images. A blood image showing a blood spot is extracted from the acquired images. The excretion start time is determined, based on the extracted excrement image. The blood appearance start time and the blood size are determined from the extracted blood image. Excretion information including the excretion start time, the blood appearance start time, and the blood size is output.

Hence, a manager of an excreter can confirm the preceding and subsequent time relation between the excretion start time and the blood appearance start time, and the blood size from the excretion information, and further distinguish types of bleeding from the confirmation result. This configuration therefore enables output of information necessary for determining whether the blood appearance or bleeding at excretion derives from bleeding attributed to an injury around an annus, or bleeding attributed to a problem in a bladder, a urinary tract, or a digestive system.

In the output device, the second determination part may further determine, based on the blood image, a color of the blood spot, and the excretion information may include color information about the determined color of the blood spot.

According to this configuration, since the color of the excrement is shown, output of information useful for grasping a possible disease of the excreter in addition to the type of the bleeding is achieved.

In the output device, the first determination part may determine, based on the color of the blood spot and the blood size, a type of the excrement, and the excretion information may include the determined type of the excrement.

This configuration outputs the type of the excrement determined based on the color of the blood spot and the blood size, and thus can present the type of the excrement that is useful for grasping the possible disease of the excreter.

In the output device, the type of the excrement may include reddish excrement and blackish excrement.

For instance, when a large intestine has a problem, there is a feature that reddish excrement containing vivid reddish blood is likely to be excreted. When other digestive system, such as a small intestine and a duodenum located at a deeper position than the large intestine, has a problem, there is a feature that blackish excrement containing blackish blood is likely to be excreted. According to this configuration, since the excrement is shown as reddish excrement or blackish excrement, output of information useful for specifying a breeding portion is achieved.

In the output device, the second extraction part may extract, from the images, a region having a predetermined number of or more continuous pixels constituting the blood spot and each having a predetermined pixel value as the blood image.

This configuration extracts the region having the predetermined number of or more continuous pixels constituting the blood spot and each having the predetermined pixel value as a blood image. Thus, the configuration can prevent a certain object or noise which is, for example, unlikely to be a blood spot regardless of its color similar to that of the blood spot from being extracted as a blood image.

In the output device, the second determination part may determine, based on the blood image, a form of the blood spot, and the excretion information may include form information about the form of the blood spot.

According to this configuration, the form of the blood spot is shown, and output information useful for the manager to determine a possible disease of the excreter is achieved.

In the output device, the form of the blood spot may include a linear form and a dot form.

For instance, a stool containing a blood spot having a linear form is likely to be excreted when the digestive system has a polyp, and a stool containing a blood spot having a dot form is likely to be excreted when hemorrhoids occur. This configuration outputs the form information indicating the linear form or the dot form of the excrement, and therefore, can output information useful for accurately determining the polyp and the hemorrhoids.

In the output device, the first extraction part may extract, from each of the images, a specific area being a predetermined area including a drain hole of the toilet, and extract the excrement image in the specific area.

This configuration can extract the excrement image focused on the specific area including the drain hole and having a high possibility of existence of the excrement, and thus can aim at optimization of the process.

In the output device, the second extraction part may extract, from each of the images, a specific area being a predetermined area including a drain hole of the toilet, and extract the blood image in the specific area.

This configuration can extract the blood image focused on the specific area including the drain hole and having a high possibility of existence of a blood spot, and thus can aim at optimization of the process.

In the output device, the output part may output the excretion information to a server when it is determined, based on sitting data output from a sitting sensor to detect sitting of an excreter on the toilet, that the excreter leaves the toilet.

This configuration outputs the excretion information at the detection of the leaving from the seat, and thus can more effectively output the excretion information while achieving a greater reduction in a communication load than a configuration of outputting excretion information per image. In addition, the configuration permits the server to manage the excretion information, and further can save the memory source of the output device.

A method according to another aspect of the disclosure is a method for an output device that outputs excretion information. The method includes: acquiring a plurality of images chronologically captured by a camera located to photograph an inside of a bowl of a toilet, each of the images including time information indicating a photographing time; extracting, from the acquired images, an excrement image showing excrement; extracting, from the acquired images, a blood image showing a blood spot; determining, based on time information about the excrement image, an excretion start time, when the extraction image is extracted; determining, based on time information about the blood image, a blood appearance start time, and determines, based on the blood image, a blood size indicating a size of the blood spot, when the blood image is extracted; and outputting, as the excretion information, information including the excretion start time, the blood appearance start time, and the blood size.

According to this configuration, it is possible to provide a method that exerts the same operational effects as those of the output device.

A program according to further another aspect of the disclosure is a program for an output device that outputs excretion information, and includes causing a processor included in the output device to execute: acquiring a plurality of images chronologically captured by a camera located to photograph an inside of a bowl of a toilet, each of the images including time information indicating a photographing time; extracting, from the acquired images, an excrement image showing excrement; extracting, from the acquired images, a blood image showing a blood spot; determining, based on time information about the excrement image, an excretion start time, when the extraction image is extracted; determining, based on time information about the blood image, a blood appearance start time, and determines, based on the blood image, a blood size indicating a size of the blood spot, when the blood image is extracted; and outputting, as the excretion information, information including the excretion start time, the blood appearance start time, and the blood size.

According to this configuration, it is possible to provide a program that exerts the same operational effects as those of the output device.

Additionally, according to this disclosure, it goes without saying that the computer program is distributable as a non-transitory computer readable storage medium like a CD-ROM, or distributable via a communication network like the Internet.

Each of the embodiments which will be described below represents a specific example of the disclosure. Numeric values, shapes, constituent elements, steps, and the order of the steps described below are mere examples, and thus should not be construed to delimit the disclosure. Moreover, constituent elements which are not recited in the independent claims each showing the broadest concept among the constituent elements in the embodiments are described as selectable constituent elements. The respective contents are combinable with each other in all the embodiments.

EMBODIMENT

FIG. 1 is a block diagram showing an example of an overall configuration of an excretion management system 1 according to an embodiment of this disclosure. The excrement management system 1 is introduced into a facility, such as an elderly care facility and a hospital, for managing a state of excrement of a user who uses the facility. Examples of the user include a care receiver who receives care in an elderly care facility and a patient who is medically treated in a hospital.

The excrement management system 1 includes an output device 2, a server 3, a display device 4, and a sensor unit 5. The output device 2, the server, 3, and the display device 4 are communicably connected to one another via a network NT. The network NT includes, for example, a wide area network having an internet communication network and a mobile phone communication network. The output device 2 and the sensor unit 5 are provided at a toilet and communicably connected to each other via a communication channel 6. Examples of the communication channel 6 includes the Bluetooth (registered trademark), an infrared communication, and a near field communication, such as the NFC. The communication channel 6 may be a wired communication channel.

The output device 2 acquires sensing data acquired by the sensor unit 5 via the communication channel 6. The output device 2 analyzes the sensing data, generates excretion information to be described later, and sends the generated excretion information to the server 3. The server 3 generates excretion history information including the received excretion information, and stores the generated excretion history information in an excretion history database to be described later. The display device 4 acquires, if necessary, the excretion history information from the server 3 via the network NT, generates a display image to be described later from the excretion history information, and displays the generated display image on a display thereof. The sensing data contains an image to be described later and sitting data.

The server 3 includes, for example, a cloud server including one or more computers. The display device 4 includes, for example, a computer owned by the manager. The display device 4 may include, for example, a stationary computer, a smartphone, or a tablet computer. Examples of the manager include a caregiver or carer, a care manager of a care receiver, or a doctor in charge of a medical treatment for a patient.

Figure 2:
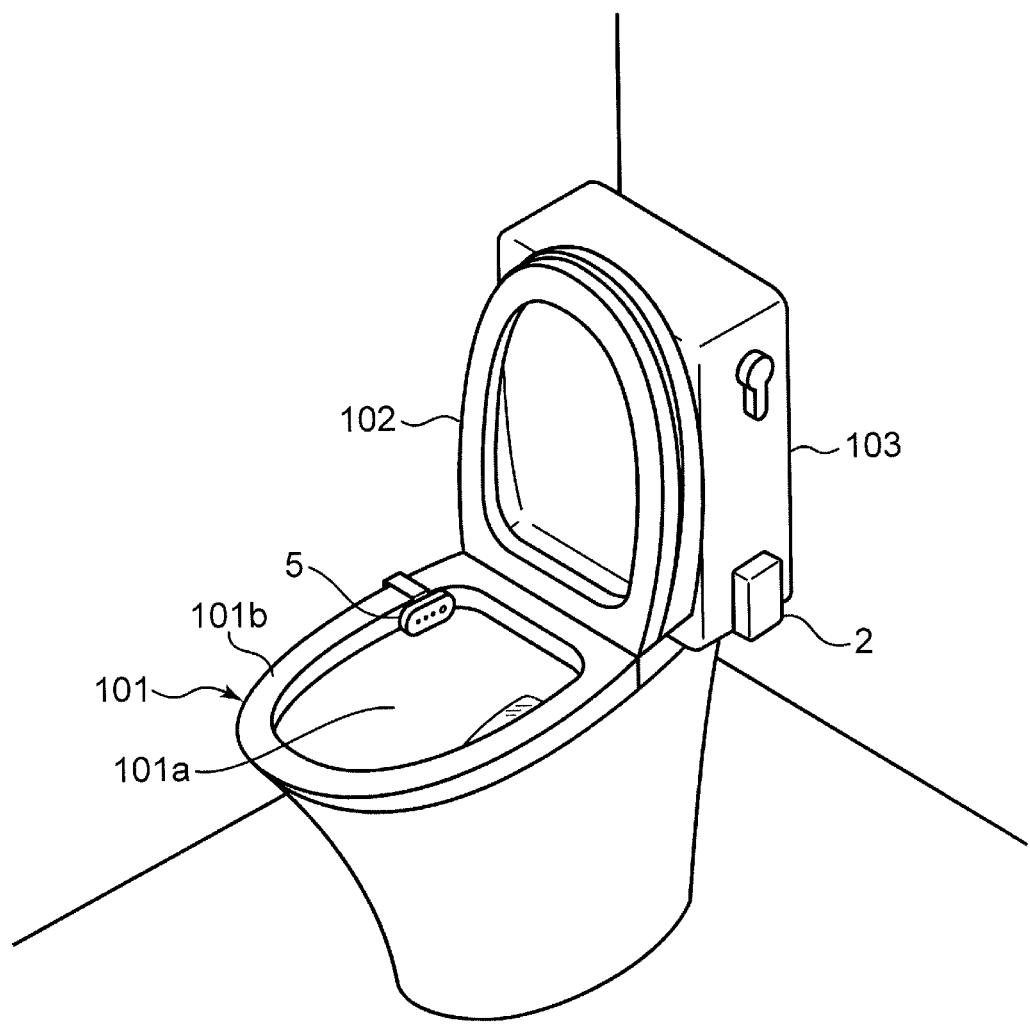
FIG. 2 is a view explaining arrangement positions of a sensor unit and an output device in the embodiment of the disclosure.

FIG. 2 is a view explaining arrangement positions of the sensor unit 5 and the output device 2 in the embodiment of the disclosure. As shown in FIG. 2, the toilet 101 includes a bowl 101a and a fringe part 101b. The fringe part 101b is located at an upper end of the toilet 101 and defines an opening section of the toilet 101. The bowl 101a is located below the fringe part 101b to receive excrement. The sensor unit 5 is attached on the fringe part 101b.

The bowl 101a has a bottom provided with an unillustrated drain hole. Excrement excreted in the bowl 101a is caused to flow to a sewage pipe through the drain hole. In other words, the toilet 101 is in the form of a toilet of a flush type. Moreover, a toilet seat 102 is provided on a top of the toilet 101 to allow a user to sit thereon. The toilet seat 102 is rotatable upward and downward. The user sits on the toilet seat 102 lowered to lie on the toilet 101. A water reservoir tank 103 that stores flush water to cause the excrement to flow to the sewage is provided in the rear of the toilet 101.

Figure 3:
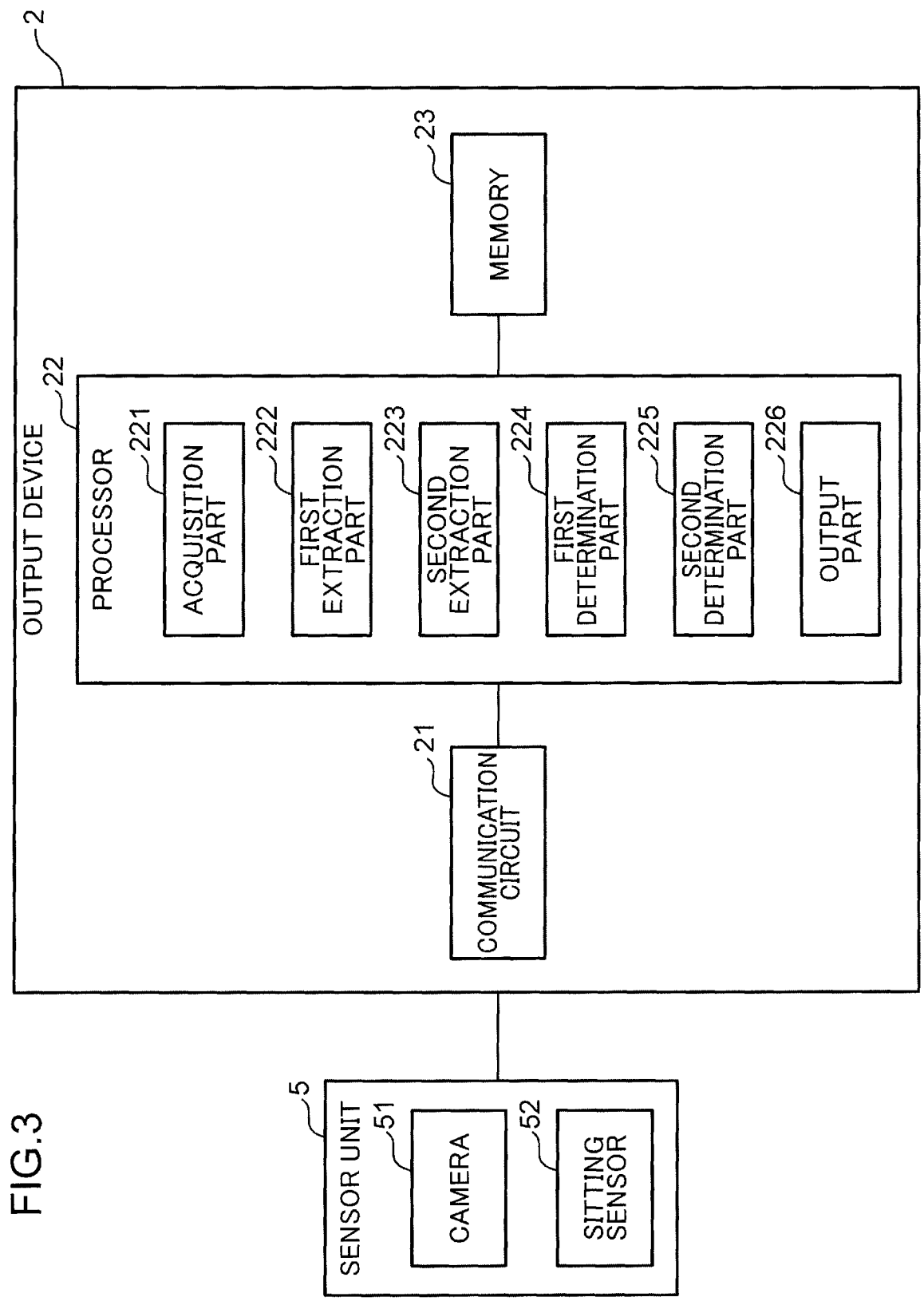
FIG. 3 is a block diagram showing an example of a configuration of the output device and the sensor unit shown in FIG. 1.

FIG. 3 is a block diagram showing an example of a configuration of the output device 2 and the sensor unit 5 shown in FIG. 1. The sensor unit 5 has a camera 51 and a sitting sensor 52. The camera 51 is located at the toilet 101 to capture an image of the bowl 101a. For instance, the camera 51 has a high sensitivity and a wide angle, and is configured to capture a color image having three color components of an R (red) component, a G (green) component, and a B (blue) component. However, this is a mere example, and the camera 51 may be a black-and-white or monochrome camera. A camera for capturing an image of an object by irradiating the object with an infrared light emitting diode and a white light emitting diode is universally used in a field of detecting objects. However, such a conventional camera faces difficulty in detecting, in particular, an object having many red-based color components. Therefore, it is difficult to distinguish stool and urine from each other. From this perspective, a camera having a high sensitivity and a wide angle is adopted as the camera 51 in the embodiment. Specifically, the camera 51 includes a CMOS having a size of one fourth inch with a high sensitivity. The camera 51 is in the form of a wide-angle camera having a horizontal view angle of 120 degrees and a vertical view angle of 100 degrees. The numerical value of each of the inches and the view angles shows a mere example, and another numerical value is adoptable. The camera 51 photographs an inside of the bowl 101a at a predetermined frame rate, adds time information indicating a photographing time to a captured image, and transmits the image including the time information to the output device 2. The time information includes, for example, time units of hour, minute, second, date, month, and year, such as, "at 15:00:00, on Apr. 1, 2021". However, this is a mere example, and thus the time information may include time units of hour, minute, and second.

The sitting sensor 52 detects whether the user sits on the toilet seat 102. The sitting sensor 52 includes, for example, an illuminance sensor which detects an illuminance of a periphery of a bowl 101a, and a distance measurement sensor which detects a distance to a certain object at the periphery of the bowl 101a. When the user sits on a toilet seat 102, the opening section is closed by the buttocks of the user, and therefore, the periphery of the bowl 101a gets dark, and thus it is determined that an object exists in the vicinity of a sensor unit 105. In this way, use of the illuminance sensor and the distance measurement sensor leads to achievement of detecting whether the user sits on the toilet seat 102. The sitting sensor 52 may include a pressure sensor which detects a pressure of the user on the toilet seat 102, in place of the illuminance sensor and the distance measurement sensor. When the sitting sensor 52 includes the pressure sensor, the sitting sensor 52 is disposed at the toilet seat 102. Alternatively, the sitting sensor 52 may include either the illuminance sensor or the distance measurement sensor. The sitting sensor 52 detects sitting or not sitting of the user at a predetermined sampling rate, and always outputs sitting data indicating a detection result to the output device 2.

The output device 2 includes a communication circuit 21, a processor 22, and a memory 23. The communication circuit 21 connects the output device 2 to the network NT and the communication channel 6. The communication circuit 21 receives an image transmitted from the camera 51 at a predetermined frame rate. The predetermined frame rate has a certain value falling within a range of, for example, 1 to 120 fps. The communication circuit 21 receives the sitting data transmitted from the sitting sensor 52 at a predetermined frame rate. The communication circuit 21 transmits the excretion information to the server 3.

For instance, the processor 22 includes a central processing unit, and has an acquisition part 221, a first extraction part 222, a second extraction part 223, a first determination part 224, a second determination part 225, and an output part 226. Each of the acquisition part 221 to the output part 226 may be realized when the processor 22 executes a predetermined program, or may be established in the form of a dedicated hardware circuit.

The acquisition part 221 acquires, by using the communication circuit 21, a plurality of images chronologically captured by the camera 51. The acquisition part 221 acquires the sitting data by using the communication circuit 21.

The first extraction part 222 extracts, from the images acquired by the acquisition part 221, an excrement image showing excrement. Here, the first extraction part 222 may extract, from each of the images, a region having a predetermined number of or more continuous pixels constituting the excrement and each having a predetermined pixel value as the excrement image. The excrement includes stool and urine. However, in the following description, the excrement is described as stool for convenience. The term "pixels constituting the excrement and each having a predetermined pixel value" represents a pixel having a pixel value falling within a predetermined range of a pixel value of each of color components indicating excrement. The color components include, for example, R (red), G (green), and B (blue). The term "pixel value of each of color components" means each of a pixel value of "R", a pixel value of "G", and a pixel value of "B". Hereinafter, the "pixel value of each of color components" is referred to as an "RGB value". The predetermined range represents a range of the RGB value predetermined as indicating excrement. The "predetermined number" means a pixel number corresponding to a smallest size of possible excrement.

The second extraction part 223 extracts, from the images acquired by the acquisition part 221, a blood image showing a blood spot. Here, the second extraction part 223 may extract, from a specific area in each of the images, a region having a predetermined number of or more continuous pixels constituting the blood spot and each having a predetermined RGB value as the blood image. The term "pixels constituting the blood spot and each having a predetermined RGB value" represents a pixel having an RGB value falling within a predetermined range for a predetermined RGB value indicating the blood spot. The predetermined range represents a range of the RGB value predetermined as indicating the blood spot. Meanwhile, the blood spot distributes in a dot form regarding an injury like hemorrhoids. In this respect, a plurality of blood images may be extracted from one image.

When the first extraction part 222 extracts an excrement image, the first determination part 224 determines, based on time information about the extracted excrement image, an excretion start time. The term "time information about the excrement image" represents time information included in the image subjected to extraction of the excrement image.

When the second extraction part 223 extracts a blood image, the second determination part 225 determines, based on time information about the blood image extracted by the second part 223, a blood appearance start time, and determines, based on the blood image, a blood size indicating a size of the blood spot. The term "time information about the blood image" represents time information included in the image subjected to the extraction of the blood image.

The output part 226 generates excretion information including the excretion start time, the blood appearance start time, and the blood size. The output part 226 gives the generated excretion information a time stamp and a user ID, and outputs the excretion information given the time stamp and the user ID to the server 3 by using the communication circuit 21. The time stamp includes an excretion start time and an excretion finish time. The user ID is an identifier identifying an excreter. The user ID may include, for example, data input by the user at sitting thereof, or data predetermined for the toilet 101.

Figure 4:
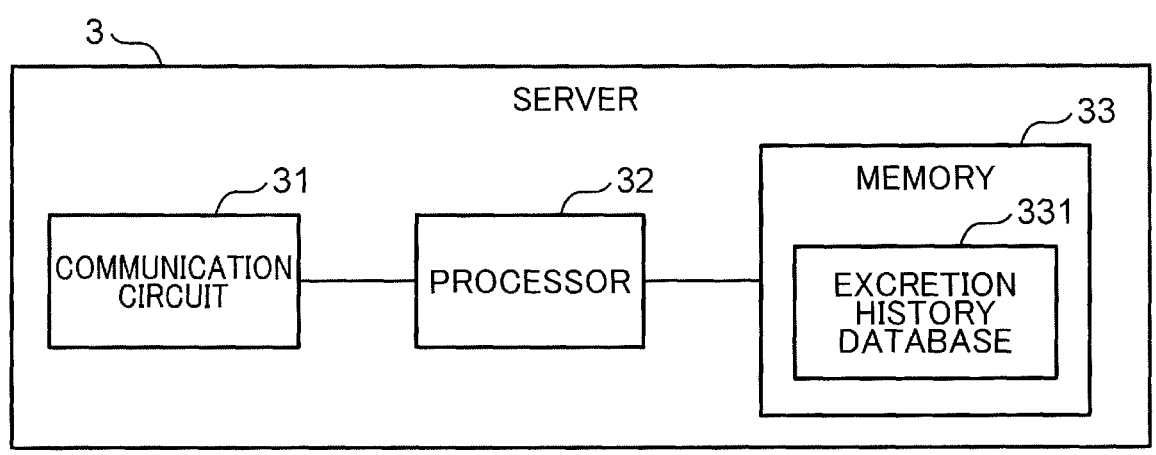
FIG. 4 is a block diagram showing an example of a configuration of a server.

FIG. 4 is a block diagram showing an example of a configuration of the server 3. The server 3 includes a communication circuit 31, a processor 32, and a memory 33. The communication circuit 31 connects the server 3 to the network NT. The processor 32 includes, for example, a CPU, and controls the entirety of the server 3. For instance, the processor 32 acquires excretion information from the output device 2 by using the communication circuit 31, generates excretion history information from the received excretion information, and stores the generated excretion history information in an excretion history database 331. The excretion history information includes the user ID, the time stamp, and the excretion information.

The memory 33 includes a non-volatile storage device, such as a solid state drive or a hard disk drive, and stores the excretion history database 331. The excretion history database 331 is a database which stores one piece of the excretion history information for one record.

Figure 5:
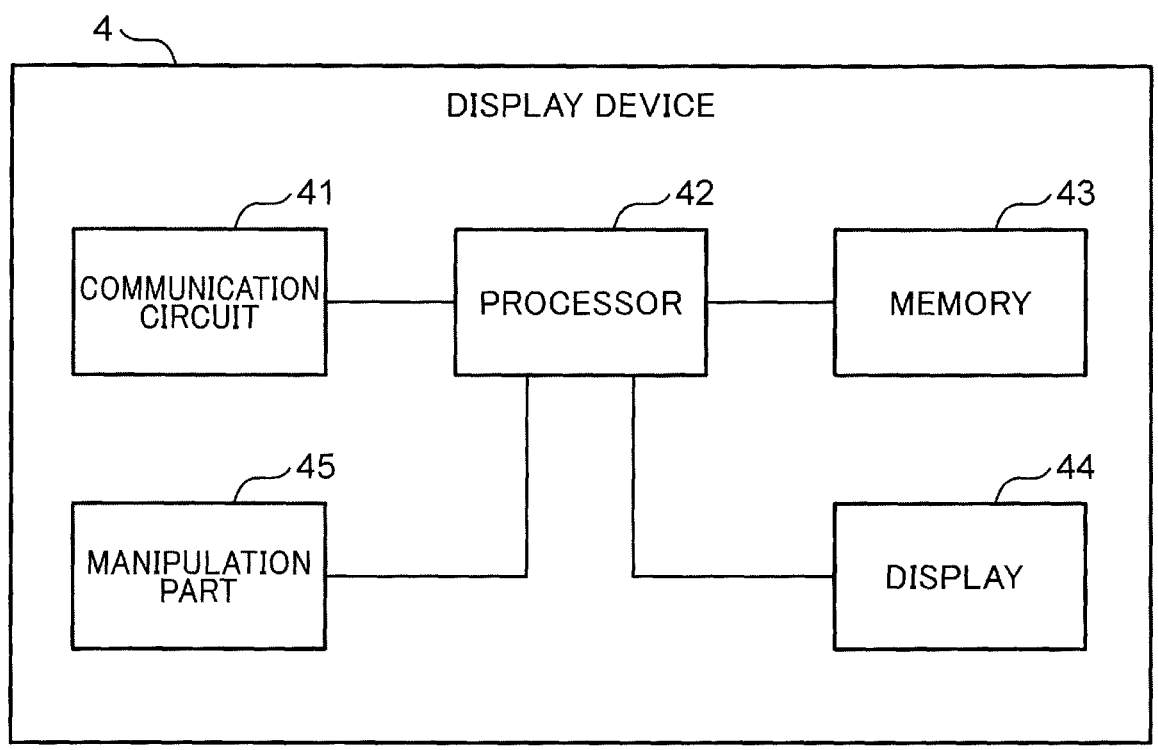
FIG. 5 is a block diagram showing an example of a configuration of a display device.

FIG. 5 is a block diagram showing an example of a configuration of the display device 4. The display device 4 includes a communication circuit 41, a processor 42, a memory 43, a display 44, and a manipulation part 45. The communication circuit 41 connects the display device 4 to the network NT. The communication circuit 41 receives the excretion history information from the server 3.

The processor 42 includes, for example, a CPU, and acquires the excretion history information transmitted from the server 3 by using the communication circuit 41, generates, based on the excretion information included in the acquired excretion history information, a display image, and displays the generated display image on the display 44. Consequently, the manager can confirm the excretion information of the user.

The memory 43 includes a rewritable non-volatile storage device, e.g., flash memory.

The display 44 includes, for example, a display device, such as a liquid crystal display panel and an organic EL panel.

The manipulation part 45 includes a keyboard, a mouse, and a touch screen for receiving an instruction from a user.

Figure 6:
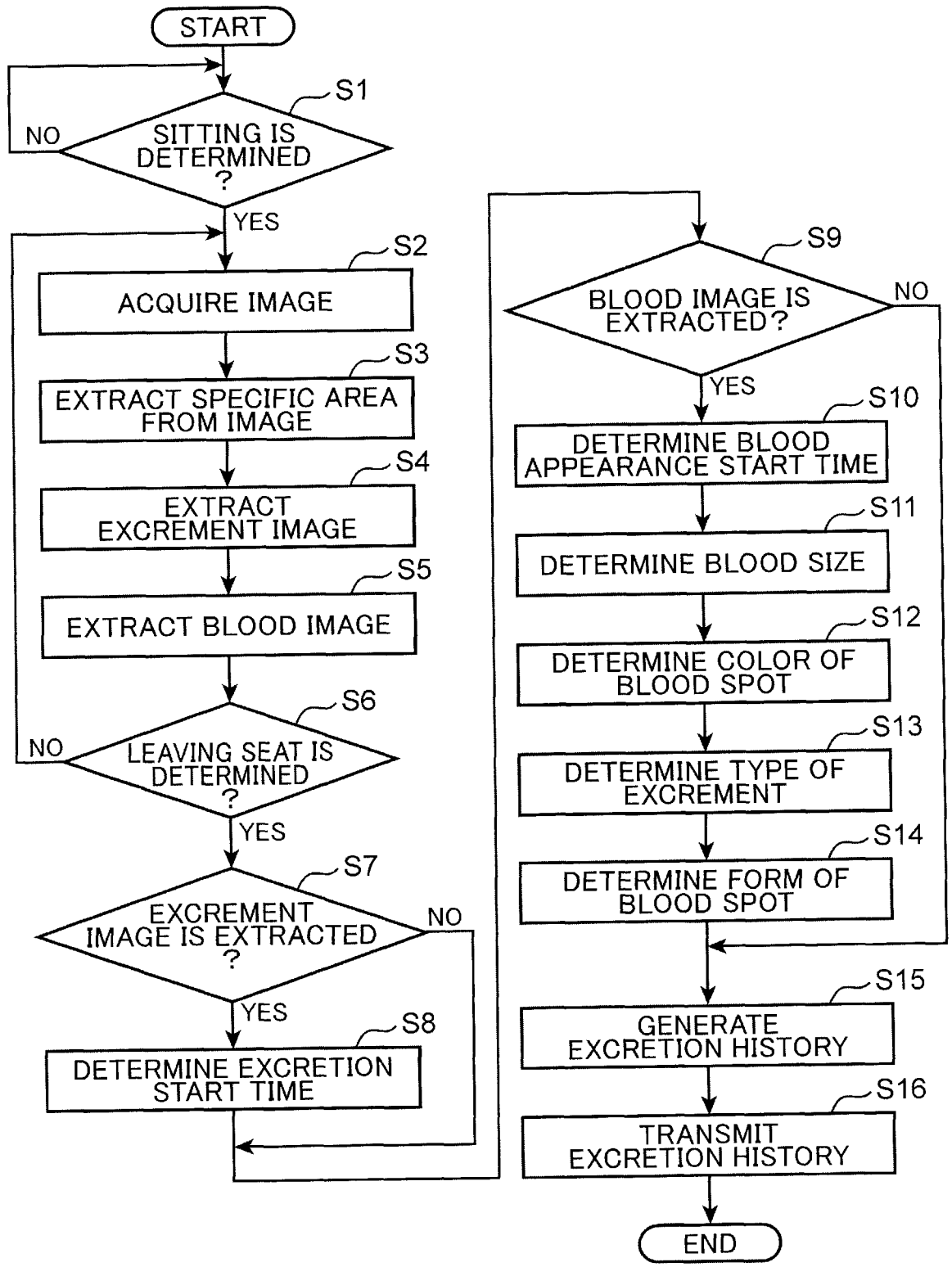
FIG. 6 is a flowchart showing an example of a process by the output device in the embodiment of the disclosure.

Heretofore, the configuration of the excrement management system 1 is described. Next, a process by the excrement management system 1 will be described. FIG. 6 is a flowchart showing an example of a process by the output device 2 according to the embodiment of the disclosure.

In step S1, the acquisition part 221 determines, based on sitting data, whether a user sits on the toilet 101. For instance, the sitting data contains "ON" data indicating the sitting when the user sits on the toilet. Further, the sitting data contains "OFF" data indicating non-sitting when the user does not sit on the toilet. Hence, the acquisition part 221 may determine that the user sits on the toilet when the sitting data contains the "ON" data, and determine that the user does not sit on the toilet when the sitting data contains the "OFF" data.

When it is determined that the user sits on the toilet 101 (YES in step S1), the acquisition part 221 acquires an image from the camera 51 (step S2). Contrarily, when it is determined that the user does not sit on the toilet 101 (NO in step S1), the process waits in step S1.

Figure 8:
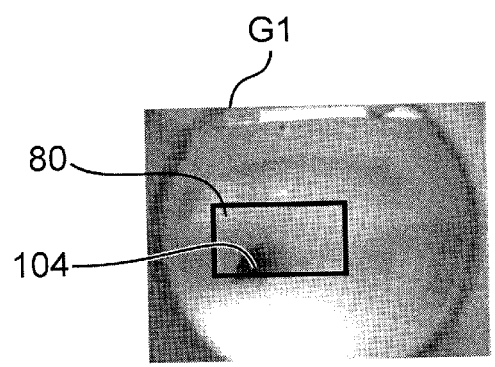
FIG. 8 shows an example of a specific area.

In step S3, the first extraction part 222 extracts, from the image acquired in step S2, a specific area. FIG. 8 shows an example of a specific area 80. As shown in FIG. 8, the specific area 80 represents a quadrangular area including a whole or part of a drain hole 104 on an image G1. On the image G1, a coordinate of the specific area 80 is predetermined from an attachment position and a view angle of the camera 51. This achieves extraction of each of an excrement image and a blood image by focusing on a region having a high possibility of existence of each of excrement and a blood spot, and hence leads to optimization of the process.

Figure 9:
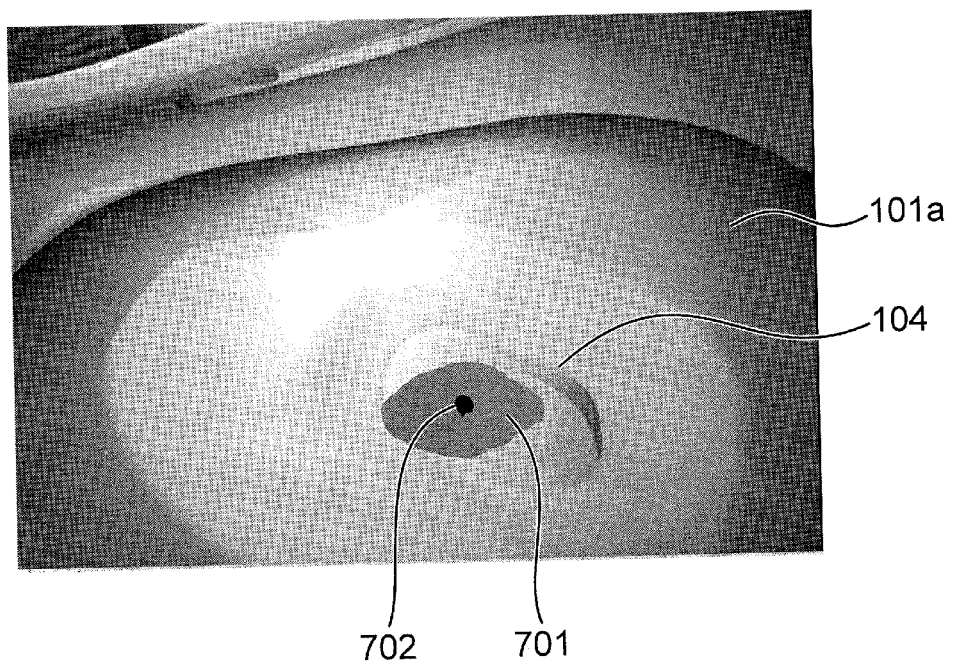
FIG. 9 shows an example of a bowl in a state of having excrement.

In step S4, the first extraction part 222 extracts, in the specific area 80, a region having a predetermined number of or more continuous pixels constituting the excrement and each having a predetermined RGB value as the excrement image. FIG. 9 shows an example of the bowl 101a in a state of having excrement 701. In the example shown in FIG. 9, the excrement 701 has been excreted around the drainage hole 104. The excreter has bleeding, and therefore, the excrement 701 has a blood spot 702 almost at the center thereof. An image obtained by photographing this state includes a predetermined number of or more continuous pixels constituting the excrement 701 and each having a predetermined RGB value. An excrement image showing excrement 70 is extracted from the acquired image.

Referring back to FIG. 6, in step S5, the second extraction part 223 extracts, in the specific area 80, a region having a predetermined number of or more continuous pixels constituting the blood spot and having a predetermined RGB value as the blood image. In the example shown in FIG. 9, the excrement 701 contains the blood spot 702 almost at the center thereof, and therefore, an image obtained by photographing this state includes a predetermined number of or more continuous pixels constituting the blood spot 702 and each having a predetermined RGB value. A blood image showing the blood spot 702 is extracted from the acquired image.

In step S6, the output part 226 determines, based on the sitting data, whether the user leaves the toilet. When the data contained in the sitting data changes from "ON" data to "OFF" data, the output part 226 may determine that the user leaves the toilet.

When it is determined that the user does not leave the toilet (NO in step S6), the process returns to step S2, and steps S2 to S5 are subjected onto a subsequent image. Contrarily, when it is determined that the excreter leaves the toilet (YES in step S6), the process proceeds to step S7.

In step S7, the first determination part 224 determines whether an excrement image is extracted in step S4. The process proceeds to step S8 when the excrement image is extracted (YES in step S7), and the process proceeds to step S9 when no excrement image is extracted (NO in step S7).

In step S8, the first determination part 224 determines an excretion start time based on time information about the excrement image extracted from the image acquired in a period (hereinafter, referred to as an "excretion period") from the sitting on and leaving from the toilet by the user. Here, the first determination part 224 may determine an earliest photographing time as the excretion start time among photographing times indicated by time information about one or more excrement images extracted in the excretion period.

In step S9, the second determination part 225 determines whether a blood image is extracted in step S5. The process proceeds to step S10 when the blood image is extracted (YES in step S9), and the process proceeds to step 15 when no blood image is extracted (NO in step S9).

In step S10, the second determination part 225 determines, based on time information about the blood image extracted from the images acquired in the excretion period, a blood appearance start time. Here, the second determination part 225 determines an earliest photographing time as the blood appearance start time among photographing times indicated by time information about one or more blood images extracted in the excretion period.

In step S11, the second determination part 225 counts the number of pixels constituting a blood image for each blood image extracted from the image acquired in the excretion period, and determines the number of pixels constituting the blood image as a blood size. Here, when the blood image is extracted from each of the images acquired in the excretion period, a blood size may be determined for each of the images. Alternatively, when a plurality of blood images is extracted from a specific target image, the second determination part 225 may determine the total pixel number of the blood images as a blood size.

In step S12, the second determination part 225 determines, based on the blood image extracted from the image acquired in the excretion period, a color of the blood spot. Here, when the blood image is extracted from each of a plurality of images acquired in the excretion period, the second determination part 225 may determine the color of the blood spot for each of the images.

In the embodiment, the color of the blood spot is classified into a first color group including a plurality of reference colors showing reddish excrement and a second color group including a plurality of reference colors showing blackish excrement. The memory 23 stores an RGB value of each reference color forming the first color group. The memory 23 stores an RGB value of each reference color forming the second color group. The second determination part 225 may determine the color of the blood spot in a manner described below.

First, the second determination part 225 may calculate an RGB average value being an average value of RGB values of respective pixels constituting a blood image extracted from a target image. Here, the RGB average value includes an average value of R, an average value of G, and an average value of B respectively forming the blood image. Subsequently, the second determination part 225 determines, as the color of the blood spot, a reference color that is most approximate to the calculated RGB average value from among the reference colors stored in the memory 23. For instance, the second determination part 225 may determine, as the color of the blood spot, a reference color having a shortest distance (e.g., the Euclidean distance) between the calculated RGB average value and an RGB average value of each of the reference colors stored in the memory 23.

In step S13, the first determination part 224 determines, based on the blood size determined in step S11 and the color of the blood determined in step S12, a type of the excrement. Here, when a blood image is extracted from each of a plurality of images acquired in the excretion period, the first determination part 224 may determine a type of excrement for each of the images.

The type of the excrement includes reddish excrement and blackish excrement. The reddish excrement represents vivid reddish stool excreted when a large intestine has a problem. The blackish excrement represents blackish and reddish stool excreted when other digestive system, such as a small intestine and a duodenum located at a deeper position than the large intestine, has a problem. Moreover, each of the reddish excrement and the blackish excrement has a size which is equal to or larger than a standard size. Therefore, the first determination part 224 may determine specific excrement as the reddish excrement when a blood size is equal to or larger than the standard size, and the color of the blood spot has a reference color in the first color group. Alternatively, the first determination part 224 may determine the excrement as the blackish excrement when the blood size is equal to or larger than the standard size, and the color of the blood spot has a reference color in the second color group.

In step S14, the second determination part 225 determines a form of the blood spot from the blood image extracted in the excretion period. The determined form of the blood spot includes a dot form and a linear form. When the digestive system has a polyp, the excrement may contain a blood spot having a linear form. Alternatively, when an injury like hemorrhoids occurs, the excrement may contain a blood spot having a dot form. Here, the second determination part 225 may determine the form of the blood spot as the linear form when at least one blood image extracted in the excretion period shows a linear form. Alternatively, the second determination part 225 may determine the form of the blood spot as the dot form when at least one blood image extracted in the excretion period shows a dot form. For instance, the second determination part 225 may apply a bounding rectangle to a specific blood image, calculate a ratio of a first side of the bounding rectangle to a second side thereof, and determine the form of the blood spot as the linear form when the calculated ratio represents a predetermined ratio indicating the linear form or higher. The first side is longer than the second side. Alternatively, when one or more blood images each having a predetermined size or smaller are extracted from a target image, the second determination part 225 may determine the form of the blood spot as the dot form.

In step S15, the output part 226 generates excretion information including blood appearance or non-blood appearance, an excretion start time, a blood appearance start time, a color of a blood spot, a type of the excrement, and a form of the blood spot. The output part 226 may make the excretion information include blood appearance in the case of "YES" in step S9 and make the excretion information include a non-blood appearance in the case of "NO" in step S9.

In step S16, the output part 226 gives the generated excretion information a user ID and a time stamp, and transmits the excretion information given the user ID and the time stamp to the server 3 by using the communication circuit 21.

Figure 7:
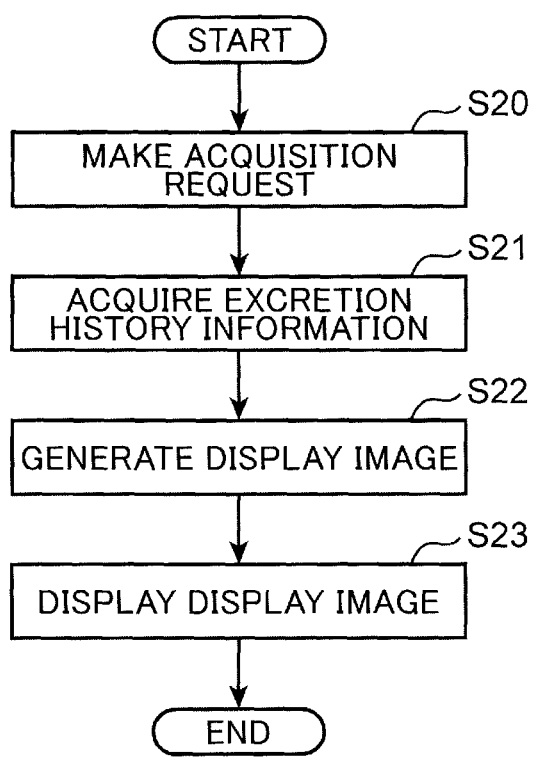
FIG. 7 is a flowchart showing an example of a process by the display device for displaying a display screen image of excretion information.

FIG. 7 is a flowchart showing an example of a process by the display device 4 for displaying a display screen image of the excretion information. In step S20, the processor 42 transmits an acquisition request for the excretion history information to the server 3 by using the communication circuit 41. Here, the manager may activate a predetermined application to cause the display 44 to display a predetermined input screen image, and manipulate the manipulation part 45 to input a necessary matter on the input screen image. The processor 42 may generate an acquisition request containing the input necessary matter and send the generated acquisition request to the server 3. Examples of the necessary matter include a user ID and a period for the excretion history information to be acquired. The server 3 having received the acquisition request acquires, from the excretion history database 331, the excretion history information corresponding to the user ID and the period contained in the acquisition request, and transmits the acquired excretion history information to the display device 4.

In step S21, the processor 42 acquires the excretion history information by using the communication circuit 41. In this manner, the processor 42 can acquire excretion information in the relevant period for a user having the user ID. Here, it is presumed that excretion information corresponding to certain one-time excretion is acquired.

In step S22, the processor 42 generates a display screen image based on the excretion information. In step S23, the processor 42 displays the display screen image on the display 44.

Figure 10:
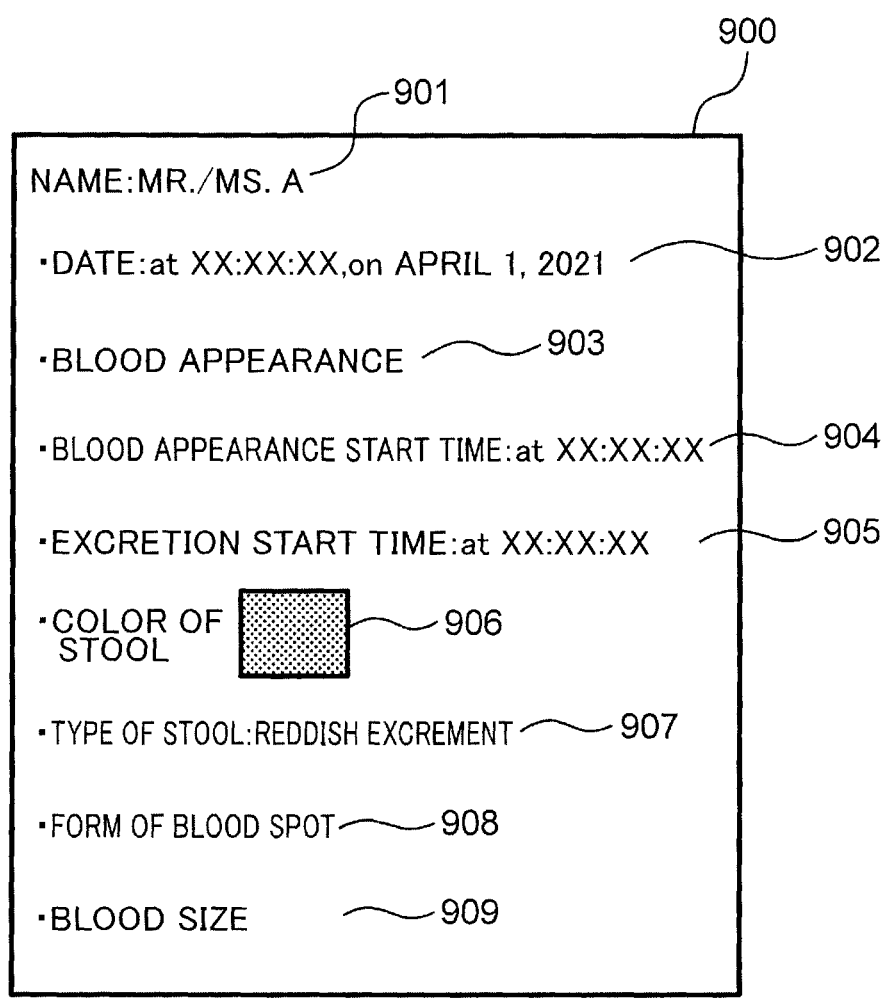
FIG. 10 shows the display screen image displayed on a display of the display device.

FIG. 10 shows a display screen image 900 displayed on the display 44 of the display device 4. The display screen image 900 has display sections 901 to 909. The display section 901 shows a name of a relevant user. The display section 902 shows an excretion date and time. The display section 903 shows blood appearance or non-blood appearance. Here, the excretion information includes information about blood appearance, and therefore, "BLOOD APPEARANCE" is shown. The display section 904 shows a blood appearance start time. The display section 905 shows an excretion start time. The display section 906 shows a color of stool (excrement). Here, when a blood image is extracted from each of a plurality of images acquired in the excretion period, the display section 906 may show a reference color having the maximum extraction frequency among reference colors each representing a color of the blood spot in each of the images. Alternatively, the color of the blood spot to be displayed in the display section 906 among the colors of the blood spot for each of the images may be changed in response to a manipulation by the manager. Alternatively, the color of the blood spot to be displayed in the display section 906 among the colors of the blood spot for each of the images may be automatically changed. Here, a panel section showing the color of the excrement is displayed. Consequently, the user can easily confirm the color of the excrement.

The display section 907 shows a type of excrement (stool). Here, the type of the stool is reddish excrement, and thus is displayed as "REDDISH STOOL". When a blood image is extracted from each of the images acquired in the excretion period, the display section 907 may show a type of excrement having the maximum extraction frequency among the types of excrement for each of the images. When, the way of changing the color of the stool to be displayed in the display section 906 is adopted, the type of the stool to be displayed in the display section 907 may be changed concurrently with changing the color.

The display section 908 shows a form of the blood spot. Here, the form of the blood spot meets neither the linear form nor the dot form, and thus the display section 908 is blank.

The display section 909 shows a blood size. When a blood image is extracted from each of a plurality of images in the excretion period, the display section 909 may show, as the blood size, an average value of blood sizes on the images. When the way of changing the color of the stool to be displayed in the display section 906 is adopted, the blood size to be shown in the display section 909 may be changed concurrently with changing the color of the stool.

The display screen image 900 shows a blood appearance start time and an excretion start time. Hence, the manager can determine that bleeding is attributed to a problem in a digestive system when, for example, the blood appearance start time precedes the excretion start time and further the blood size is larger. Moreover, in this case, it is possible to determine that bleeding occurs at the large intestine or at a deeper position than the large intestine with reference to the type of the excrement (stool) shown in the display section 907 and the color of the excrement (stool) shown in the display section 906.

By contrast, the manager can determine that bleeding is attributed to an injury like hemorrhoids when the blood appearance start time follows the excretion start time and the blood size is smaller.

As described heretofore, according to the embodiment, it is possible to present information necessary for determining whether bleeding at excretion is attributed to an injury or a problem in a digestive system before the manager.

This disclosure can adopt modifications described below.

Although the type of excrement includes reddish excrement and blackish excrement in the embodiment, this disclosure is not limited thereto. The type of the excrement may include greenish excrement and whitish excrement. In this case, when a distance between a color of an excrement image extracted by the first extraction part 222 and a predetermined reference color indicating greenish excrement as stored in the memory 23 has a threshold or lower, the first determination part 224 may determine the type of the excrement as the greenish excrement. Alternatively, when a distance between a color of an excrement image extracted by the first extraction part 222 and a predetermined reference color indicating whitish excrement as stored in the memory 23 has a threshold or lower, the first determination part 224 may determine the type of the excrement as the whitish excrement. The whitish excrement may be excreted in rotavirus infection. The greenish excrement may be excreted in enterovirus infection.

(2) In the embodiment, the server 3 may transmit alert information to the display device 4 of the manager who manages the relevant user when receiving excretion information including a blood size equal to or larger than a predetermined size indicating a problem in a digestive system. Adoptable ways of transmitting the alert information includes push notification. The display device 4 having received the alert information gives push notification for the alert information. Consequently, the manager can rapidly grasp the problem of the relevant user and can make an appropriate treatment.

(3) In the embodiment, the output part 226 may add images of the specific area 80 acquired in the excretion period to the excretion information. In this case, the display device 4 having received the excretion information may chronologically change images of the specific area 80 included in the received excretion information to be displayed on the display screen image 900. Further in this case, the display device 4 may change the displaying of the color of the stool to be displayed in the display section 906 concurrently with changing the image of the specific area 80 to be displayed on the display screen image 900.

(4) In the embodiment, the excrement may include urine. In this case, a urine excretion start time is adopted as the excretion start time. Moreover, when the excrement includes both the urine and stool, the first determination part 224 may determine an excretion start time of each of the urine and the stool. The first extraction part 222 extracts a region having a predetermined number of or more continuous pixels constituting the urine and each having a predetermined RGB value as a urine image. When the urine image is extracted, the first determination part 224 may determine, as a urination stat time, an earliest photographing time among photographing times indicated by time information about urine images extracted in an excretion period.

(5) The output part 226 may generate information indicating which precedes whether the excretion start time or the blood appearance start time, and add the generated information to the excretion information. In this case, the output part 226 may generate information indicating which time is earlier than the other and how earlier the time is, and add the generated information to the excretion information.

(6) In the flowchart shown in FIG. 6, when no excrement image is detected (NO in step S7) and a blood image is extracted (step S9), the second determination part 225 may determine that there is a high possibility of hematuria. In this case, the output part 226 may add information about the high possibility of hematuria to the excretion information. Consequently, it is possible to output information necessary for determining a problem in a bladder or a urinary tract.

The invention claimed is:

1. An output device for outputting excretion information, comprising:
   an acquisition part that acquires a plurality of images chronologically captured by a camera located to photograph an inside of a bowl of a toilet, each of the images including time information indicating a photographing time;
   a first extraction part that extracts, from the acquired images, an excrement image showing excrement;
   a second extraction part that extracts, from the acquired images, a blood image showing a blood spot;
   a first determination part that determines, based on time information about the excrement image, an excretion start time, when the first extraction part extracts the excrement image;
   a second determination part that determines, based on time information about the blood image, a blood appearance start time, and determines, based on the blood image, a blood size indicating a size of the blood spot, when the second extraction part extracts the blood image; and
   an output part that generates, as the excretion information, information including the excretion start time, the blood appearance start time, and the blood size, and outputs the generated excretion information.

2. The output device according to claim 1, wherein the second determination part further determines, based on the blood image, a color of the blood spot, and
   the excretion information includes color information about the determined color of the blood spot.

3. The output device according to claim 2, wherein the first determination part determines, based on the color of the blood spot and the blood size, a type of the excrement, and
   the excretion information includes the determined type of the excrement.

4. The output device according to claim 3, wherein the type of the excrement includes reddish excrement and blackish excrement.

5. The output device according to claim 1, wherein the second extraction part extracts, from the images, a region having a predetermined number of or more continuous pixels constituting the blood spot and each having a predetermined pixel value as the blood image.

6. The output device according to claim 1, wherein the second determination part determines, based on the blood image, a form of the blood spot, and
   the excretion information includes form information about the form of the blood spot.

7. The output device according to claim 6, wherein the form of the blood spot includes a linear form and a dot form.

8. The output device according to claim 1, wherein the first extraction part extracts, from each of the images, a specific area being a predetermined area including a drain hole of the toilet, and extracts the excrement image in the specific area.

9. The output device according to claim 1, wherein the second extraction part extracts, from each of the images, a specific area being a predetermined area including a drain hole of the toilet, and extracts the blood image in the specific area.

10. The output device according to claim 1, wherein the output part outputs the excretion information to a server when it is determined, based on sitting data output from a sitting sensor to detect sitting of an excreter on the toilet, that the excreter leaves the toilet.

11. A method for an output device that outputs excretion information, comprising:
    acquiring a plurality of images chronologically captured by a camera located to photograph an inside of a bowl of a toilet, each of the images including time information indicating a photographing time;
    extracting, from the acquired images, an excrement image showing excrement;
    extracting, from the acquired images, a blood image showing a blood spot;
    determining, based on time information about the excrement image, an excretion start time, when the extraction image is extracted;
    determining, based on time information about the blood image, a blood appearance start time, and determines, based on the blood image, a blood size indicating a size of the blood spot, when the blood image is extracted; and
    outputting, as the excretion information, information including the excretion start time, the blood appearance start time, and the blood size.

12. A non-transitory computer-readable recording medium storing a program for an output device that outputs excretion information, comprising:
    causing a processor included in the output device to execute:
      acquiring a plurality of images chronologically captured by a camera located to photograph an inside of a bowl of a toilet, each of the images including time information indicating a photographing time;
      extracting, from the acquired images, an excrement image showing excrement;
      extracting, from the acquired images, a blood image showing a blood spot;
      determining, based on time information about the excrement image, an excretion start time, when the extraction image is extracted;
      determining, based on time information about the blood image, a blood appearance start time, and determines, based on the blood image, a blood size indicating a size of the blood spot, when the blood image is extracted; and
      outputting, as the excretion information, information including the excretion start time, the blood appearance start time, and the blood size.

* * * * *